United States Patent [19]

Lionelle et al.

[11] 4,407,818

[45] Oct. 4, 1983

[54] ANTI VIRAL, ANTI BACTERIAL AND/OR ANTI FUNGAL COMPOSITION CONTAINING METAL OXYALKYLATE

[75] Inventors: Joseph E. Lionelle; Jeffrey A. Staffa, both of Salida, Colo.

[73] Assignee: Bio-Systems Research, Inc., Salida, Colo.

[21] Appl. No.: 304,303

[22] Filed: Sep. 21, 1981

Related U.S. Application Data

[63] Continuation of Ser. No. 217,120, Dec. 17, 1980, abandoned, which is a continuation-in-part of Ser. No. 214,103, Dec. 8, 1980.

[51] Int. Cl.³ .................... A61K 31/045; A01N 55/02
[52] U.S. Cl. .................................... 424/289; 424/343
[58] Field of Search ................................ 424/289, 343

[56] References Cited

U.S. PATENT DOCUMENTS 2,030,093  2/1936  Bausquet et al. .................. 424/301
3,367,869  2/1968  Silver et al. .......................... 252/35
4,172,841 10/1979  Danna et al. ..................... 260/429.9

OTHER PUBLICATIONS

Chemical Abstracts, 49, 12909h, (1955).
Merck Index, 9th ed., Rahway, N.J., Merck & Co., Inc., 1976, p. 931.
Barratt, et al. *Analytica Chimica Acta*, vol. 57, No. 2, pp. 447–451, (1971).

Primary Examiner—Delbert R. Phillips
Assistant Examiner—F. T. Moezie
Attorney, Agent, or Firm—Larson and Taylor

[57] ABSTRACT

An anti viral, anti bacterial and/or anti fungal composition comprises the reaction product of a metal, a carboxylic acid, and hydrogen peroxide. A typical composition comprises zinc, hexakis(acetato)oxotetra (or "zinc oxyacetate"). The composition is useful to treat several types of viruses, bacteria, and/or fungi. The zinc compound is particularly effective against Herpes virus, including Herpes simplex types I and II.

22 Claims, No Drawings

ANTI VIRAL, ANTI BACTERIAL AND/OR ANTI FUNGAL COMPOSITION CONTAINING METAL OXYALKYLATE

This application is a continuation of Ser. No. 217,120, filed 12/17/80, abandoned, which is a continuation in part of Ser. No. 214,103, filed 12/8/80.

The present invention relates to a method of treating viral, bacterial, and/or fungal infections and to an anti viral, anti bacterial and/or anti fungal composition. The invention relates particularly to a composition and method of treating Herpes Virus, including Herpes simplex virus, type I and II (hereinafter referred to as "HSV-1" and "HSV-2").

In accordance with the invention, the reaction product of a metal, a carboxylic acid, and hydrogen peroxide, such as zibnc, hexakis(acetato) oxotetra (hereinafter referred to as "zinc oxyacetate") is used to treat a virus, bacteria or fungus infection by administering an effective amount thereof to an infected patient. The compound can be administered topically or systemically, preferably in admixture with a pharmaceutical carrier. For topical use, the compound is preferably administered in an ointment or cream containing, preferably, from 0.1 to 20% by weight of the compound. For systemic use, daily dosage is generally about 15-50 mg of zinc for a person of average (70 kg) weight.

Zinc oxyacetate has the empirical formula $C_{12}H_{18}O_{13}Zn_4$ and the structural formula $Zn_4 O(CH_3CO_2)_6$ and the compound and its preparation are described in the literature. See the *Bulletin of the Chemical Society of Japan*, March 1954, Volume 27, No. 2, pp. 112–114, in which the compound is prepared by slowly distilling powdered anhydrous zinc acetate in a high vacuum. Zinc oxyacetate sublimes gradually and is collected as crystalline crust on a cool place in the distillation vessel. It is preferred, however, to make the compound in the manner described in our co-pending application Ser. No. 304,305, filed 9/21/81 and entitled "Metal Oxyalkylates, Methods of Making Same, and Uses Thereof". The disclosure of said application is herein incorporated by reference. In that method, a metal, a carboxylic acid, and hydrogen peroxide are reacted in an aqueous reaction mixture and the metal oxyalkylate precipitate is recovered. Preferred metals include zinc, beryllium, chromium, manganese, cobalt, cadmium and mercury. The structural formula for all of the compounds has not been confirmed. However, the following general formula is attributed:

$$M_{2-8}O(R-CO_2)_6$$

where M represents the metal cation, and R represents hydrogen or alkyl. The manganese and zinc compounds have been found to have the structural formula $M_4O(R-CO_2)_6$. Preferred acids include aliphatic carboxylic acids, preferably lower alkyl of up to 8 carbon atoms. Preferred acids include formic and acetic.

The Examples which follow illustrate the use of the compound as an anti virus, anti bacteria, or anti fungas agent.

EXAMPLE 1

A stock (1%) solution is prepared by dissolving 0.1 gm of zinc ocyacetate in 10 ml of water. A ½ dilution (0.5% solution) is made by admixing 5 ml of the stock solution and 5 ml of water. A ¼ dilution (0.25% solution) is made by admixing 5 ml of the 0.5% solution and 5 ml of water. A 1/10 dilution (0.1% solution) is made by admixing 1 ml of the stock (1%) solution and 9 ml of water. Fine filter paper discs of 1 cm diameter are placed in each of four clean petri dishes. In dish #1, 0.1 ml of the 1% solution is dropped onto each filter disc and allowed to air dry. The same is done in dish #2 except that the 0.5% solution is used. The same is done on dishes #3 and #4 except that the 0.25 and 0.1% solutions, respectively, are used. One ml of a previously prepared $1 \times 10^{-4}$ dilution of a broth bacterial culture (*Staphylococcus aureus*) is then spread evenly over the entire surface of four agar plates. At the 12 o'clock position on each of the agar plates, a disc from dish #1 (1% solution) is placed. Discs from dishes #2, #3 and #4 are similarly placed at the 3 o'clock, 6 o'clock, and 9 o'clock positions, respectively, of each of the four plates. Each disc is gently pressed to enure good contact with the agar surface. For comparison purposes, a further stock solution of zinc sulphate (1%) is made up and an identical series of tests made. Each plate is incubated overnight at 37° C. and the area of inhibition—the clear area around each disc—is measured.

Results are as follows:

| Compound | Plate No. | Clear Area (cm) | | | | Control |
|---|---|---|---|---|---|---|
| | | 1% | .5% | .25% | .01% | |
| Zinc oxyacetate | 1 | 1.85 | 1.70 | 1.32 | — | — |
| Zinc oxyacetate | 2 | 1.80 | 1.52 | 1.35 | — | — |
| Zinc oxyacetate | 3 | 1.78 | 1.61 | 1.40 | 1.25 | — |
| Zinc oxyacetate | 4 | 1.85 | 1.72 | 1.42 | — | — |
| Zinc oxyacetate | Average | 1.82 | 1.64 | 1.37 | 0.31 | — |
| Zinc sulphate | 1 | 1.80 | 1.50 | 1.40 | — | N/A |
| Zinc sulphate | 2 | 1.72 | 1.45 | 1.40 | 1.22 | N/A |
| Zinc sulphate | 3 | 1.71 | 1.41 | 1.39 | — | N/A |
| Zinc sulphate | 4 | 1.42 | 1.40 | 1.31 | 1.21 | N/A |
| Zinc sulphate | Average | 1.66 | 1.44 | 1.37 | 0.61 | N/A |

The results show that zinc oxyacetate has bacteriostatic qualities comparable to those of zinc sulphate. At 1% and 0.50% concentration of zinc sulphate, a visible precipitate formed under each sensitivity disc.

EXAMPLE 2

Bread mold is innoculated on a nutrient plate. Disc of filter paper prepared as in Example 1 show good growth inhibition for the undiluted material and the 1% solution. The less concentrated solution does not noticeably inhibit growth.

EXAMPLE 3

Evaluation of the compound is made using a simple neutralization of viral cytopathogenic effect (CPE) on Buffalo Green Monkey (BGM) cells using two tubes for each dilution of virus. The titer of Herpes simplex virus type 1 (HSV-1) is $10^{-4}$ based on 4+(100%) CPE, while that of HSV-2 is $10^{-2}$. In order to evaluate zinc oxyacetate, the compound (or the compound in equal weight admixture with lauryl alcohol) is incubated for 1 hour with the virus prior to making ten-fold serialdilutions and innoculating the BGM tubes. The amount of virus used is 0.1 ml. The amount of test material used is 0.1 ml of a solution containing 0.1% of Tween 80 and 0.1% of the test material.

| TEST | Titer based on 4+(100%) CPE | |
|---|---|---|
| | HSV-1 | HSV-2 |
| 1. Control | $10^{-4}$ | $10^{-2}$ |
| 2. Zinc Oxyacetate | $10^{-3}$ (1 log inhibition) | 0 (2 log inhibition) |
| 3. 50% Zinc Oxyacetate 50% lauryl alcohol | $10^{-1}$ (3 log inhibition) | 0 (2 log inhibition) |

The data shows that the compound is effective in inhibiting the virus and that the compound in admixture with the lauryl alcohol carrier is substantially more effective than the compound per se in inhibiting the more virulent HSV-1 virus.

EXAMPLE 4

In a test similar to that of Example 2, zinc oxyacetate is tested for inhibition of four bread molds. The amount of zinc oxyacetate is 0.1 ml of a 1% solution containing 0.1% Tween 80. The amount of mold is 0.1 ml. Test results are indicated in the table.

| Mold | Size of cleared area (mm) |
|---|---|
| Candida albicans | 9 |
| Trichophyton mentagrophytes | 9 |
| Microsporum canis | 8 |
| Trichophyton rubrum | 5 |

The preferred carriers, for topical use, are petrolatum and alcohols of from 8–18 carbon atoms, preferably lauryl alcohol. An admixture of petrolatum and one or more of said alcohols may be used, preferably in a weight ratio of petrolatum to alcohol of 1:10 to 10:1. A suitable admixture is petrolatum 80% and lauryl alcohol 20%, by weight.

EXAMPLES 5–11

Magnanese oxyacetate having the structural formula $Mn_4O(CH_3CO_2)_6$ is prepared as disclosed in copending application Ser. No. 304,305. In this example, the manganese compound is compared by plague assays done on HSV-1 and HSV-2 with the zinc lauryl alcohol composition of Example 3. All of the tests including those of Examples 12–17 which follow are with test substances dissolved in 2% FBS(fetal bovine serum)-MEM (Eagles Minimum Essential Medium). The solubility of the zinc containing compounds is poor and is reported as less than 1 mg/ml. The manganese compound is readily soluble and concentration is 1 mg/ml. Results are as follows:

| | | A. HSV-2 | | |
|---|---|---|---|---|
| Example | HSV-2 | Manganese Compound | Zn composition | Control |
| 5 | $10^{-1}$ | Toxic | ND[1] | ND |
| 6 | $10^{-2}$ | 4 | 0 | 39 |
| 7 | $10^{-3}$ | 0 | 0 | 5 |

[1]Not Done

As indicated in the results, both substances inhibited HSV-2. However, the manganese compound was less effective than the zinc composition.

| | | B. HSV-1 | | | | | | | | |
|---|---|---|---|---|---|---|---|---|---|---|
| | | Manganese Compound | | | Zn Composition | | | Control | | |
| Example | HSV-1 | 2%[1] | 1.5% | 0% | 2% | 1.5% | 0% | 2% | 1.5% | 0% |
| 8 | $10^{-2}$ | Irr[2] | Irr | 90 | TNC[3] | TNC | TNC | ND[4] | ND | TNC |
| 9 | $10^{-3}$ | 46 | 45 | 11 | 24 | 105 | 31 | 115 | TNC | 34 |
| 10 | $10^{-4}$ | 5 | 5 | 4 | 16 | 6 | 5 | 10 | 38 | 6 |
| 11 | $10^{-5}$ | 0 | 0 | 0 | 0 | 0 | 0 | 3 | 3 | 5 |

[1]% Methylcellulose in overlay medium (2%, 1.5% or 0%)
[2]Irregular results
[3]Too numerous to count
[4]Not done The HSV-1 does not plaque as easily as the HSV-2 strain. HSV-1 has a tendency to cause cell aggregate formation rather than distinct plaques. Consequently, two different concentrations of methylcellulose are used in the overlay medium, and finally, in the last trial a liquid overlay is used in an effort to get clear, distinct plaques. There are some variations in the results but, overall, with HSV-1, the Zn substance is less effective than the maganese compound in inhibiting HSV-1. This finding could be due to the lower solubility of the Zn material in 2% FBS-MEM.

EXAMPLES 12–14

Cytopathogenic effect (CPE) trials are carried out on the manganese compound and zinc composition of Examples 5–11. As shown in the following results, these substances are not effective against the RNA viruses Echo 5 and Polio 1:

| Example | | Echo 5 | Polio 1 |
|---|---|---|---|
| 12 | Control | $10^{-6.25(1)}$ | $10^{-7}$ |
| 13 | Manganese compound | $10^{-6.0}$ | $10^{-7.5}$ |
| 14 | Zn composition | $10^{-6.5}$ | $10^{-7.5}$ |

[1]Approximate titer on BGM cells based on 4+ (100%) CPE.

EXAMPLES 15–16

CPE trials for the Maganese compound of Examples 5–11 are conducted as in Examples 12 ∝ 14 on HSV-1 and HSV-2. As is shown in the results which follow, the manganese compound is effective against HSV-2 but is probably not effective against HSV-1. The HSV-2 data are interesting because of the apparent viristatic action of the Mn compound rather than the viricidal activity seen with the Zn compound. Apparently at $10^{-1}$ dilution of HSV-2, enough Mn compound is present to inhibit the virus completely and cause an increase in the size of the BGM cells. At $10^{-2}$ and $10^{-3}$, one tube in each dilution showed early inhibition of virus but later the virus manifested itself in the typical syncytial formation.

| Example | | HSV-1 | HSV-2 |
|---|---|---|---|
| 15 | Control | $10^{-3.5(1)}$ | $10^{-2.5}$ |
| 16 | Mn Compound | $10^{-3.0}$ | Inhibition |

[1] Approximate titer on BGM cells based on 4+ (100%) CPE.

EXAMPLE 17

CPE trials for the manganese compound and zinc composition of Examples 5-11 are connected as in Examples 12-14 on a DNA virus, Adenovirus type 4, using KB cells (human continuous cell line). The data clearly indicates that neither the test compound nor Zn carrier are effective in inhibiting the CPE of Adenvirus type 4 on KB cells. The titer in all cases in $10^{-3}$.

What is claimed is:

1. A therapeutic composition for treating Herpes virus comprising an effective amount of a metal oxyalkylate having the formula $M_4O(R-CO_2)_6$ wherein M represents zinc or manganese and R represents hydrogen or methyl, and a pharmaceutically acceptable carrier therefor.

2. A composition according to claim 1 wherein the metal oxyalkylate is present in an amount of from 0.1 to 20% by weight.

3. A composition according to claim 1 wherein said carrier comprises petrolatum.

4. A composition according to claim 1 wherein said carrier comprises an alcohol having from 8 to 18 carbon atoms.

5. A composition according to claim 4 wherein said carrier comprises lauryl alcohol.

6. A composition according to claim 1 wherein said carrier comprises petrolatum and lauryl alcohol in a weight ratio of petrolatum:lauryl alcohol of from 1:10 to 10:1.

7. A composition according to claim 6 comprising metal oxyalkylate in an amount of 10% by weight, petrolatum in an amount of 80% by weight, and lauryl alcohol in an amount of 10% by weight.

8. A composition according to claim 1 wherein said metal oxyalkylate comprises the reaction product of zinc or manganese, acetic or formic acid, and hydrogen peroxide.

9. A composition according to claim 1 wherein said metal oxyalkylate is selected from the group consisting of zinc oxyacetate and maganese oxyacetate.

10. A method of treating a Herpes virus infection comprising administering to a patient having a Herpes virus infection an effective amount of a metal oxyalkylate having the general formula $M_4O(R-CO_2)_6$ wherein M represents zinc or manganese and wherein R represents hydrogen or methyl.

11. A method according to claim 10 wherein the Herpes virus infection is topical and the metal oxyalkylate is administered topically.

12. A method according to claim 10 wherein said infection is systemic and the metal oxyalkylate is administered systemically.

13. A method according to claim 12 wherein the metal oxyalkylate is administered orally.

14. A method according to claim 11 wherein the metal oxyalkylate is administered in admixture with a pharamaceutically acceptable carrier.

15. A method according to claim 14 wherein said Herpes virus carrier comprises petrolatum.

16. A method according to claim 14 wherein said carrier comprises and alcohol having from 8 to 18 carbon atoms.

17. A method according to claim 14 wherein said carrier comprises lauryl alcohol.

18. A method according to claim 10 wherein said metal comprises zinc.

19. A method according to claim 10 wherein said metal comprises manganese.

20. A method according to claim 10 wherein said Herpes virus comprises Herpes simplex virus.

21. A method according to claim 20, wherein said Herpes simplex virus comprises HSV-1.

22. A method according to claim 20, wherein said Herpes simplex virus comprises HSV-2.

* * * * *

UNITED STATES PATENT AND TRADEMARK OFFICE
CERTIFICATE OF CORRECTION

PATENT NO. : 4,407,818
DATED : October 4, 1983
INVENTOR(S) : LIONELLE ET AL

It is certified that error appears in the above-identified patent and that said Letters Patent are hereby corrected as shown below:

In the title; column 1, line 45; Claim 1, lines 2 & 3; Claim 2, line 2; Claim 7, line 2; Claim 8, line 2; Claim 9, line 2; Claim 10, lines 3 & 4; Claim 11, lines 2 & 3; Claim 12, line 2; Claim 13, line 2; and Claim 14, line 2, delete "oxyalkylate" and insert -- oxycarboxylate --.

Column 1, line 40, delete "oxyalkylates", and insert -- oxycarboxylates --.

Signed and Sealed this

Eighth Day of January 1985

[SEAL]

Attest:

Attesting Officer

GERALD J. MOSSINGHOFF

Commissioner of Patents and Trademarks